(12) United States Patent
Zaitseva et al.

(10) Patent No.: US 8,872,125 B2
(45) Date of Patent: Oct. 28, 2014

(54) SOLUTION-GROWN CRYSTALS FOR NEUTRON RADIATION DETECTORS, AND METHODS OF SOLUTION GROWTH

(75) Inventors: Natalia Zaitseva, Livermore, CA (US); M. Leslie Carman, San Ramon, CA (US); Steve Payne, Castro Valley, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 189 days.

(21) Appl. No.: 13/477,910

(22) Filed: May 22, 2012

(65) Prior Publication Data
US 2012/0326042 A1 Dec. 27, 2012

Related U.S. Application Data

(63) Continuation-in-part of application No. 12/418,434, filed on Apr. 3, 2009, now Pat. No. 8,207,507.

(51) Int. Cl.
*G01T 3/06* (2006.01)
(52) U.S. Cl.
CPC .......................................... *G01T 3/06* (2013.01)
USPC ...................................................... 250/390.11
(58) Field of Classification Search
CPC ..................................... G01T 3/00; G01T 3/06
USPC ........................... 250/370.05, 390.01, 390.11
See application file for complete search history.

(56) References Cited

U.S. PATENT DOCUMENTS

| | | |
|---|---|---|
| 3,116,417 A | 12/1963 | Orr et al. |
| 3,817,633 A | 6/1974 | White |
| 4,482,808 A | 11/1984 | Tominaga et al. |
| 4,692,266 A | 9/1987 | Costa et al. |
| 4,957,114 A | 9/1990 | Zeng et al. |
| 5,042,494 A | 8/1991 | Alfano |
| 5,131,398 A | 7/1992 | Alfano et al. |
| 5,261,410 A | 11/1993 | Alfano et al. |
| 5,313,306 A | 5/1994 | Kuban et al. |
| 5,348,018 A | 9/1994 | Alfano et al. |
| 5,467,767 A | 11/1995 | Alfano et al. |
| 5,593,879 A | 1/1997 | Steller et al. |
| 5,726,453 A | 3/1998 | Lott et al. |
| 5,769,081 A | 6/1998 | Alfano et al. |
| 5,833,596 A | 11/1998 | Bonnell et al. |
| 5,847,394 A | 12/1998 | Alfano et al. |
| 5,940,460 A | 8/1999 | Seidel et al. |

(Continued)

FOREIGN PATENT DOCUMENTS

EP    0 352 952 A2    1/1990

OTHER PUBLICATIONS

U.S. Appl. No. 13/742,298, filed Jan. 15, 2013.
U.S. Appl. No. 13/471,259, filed May 14, 2012.

(Continued)

*Primary Examiner* — Mark R Gaworecki
(74) *Attorney, Agent, or Firm* — Dominic M. Kotab

(57) ABSTRACT

An organic crystal according to one embodiment includes an organic crystal comprising diphenylacetylene and stilbene or a stilbene derivative, the crystal having physical characteristics of formation from solution, the organic crystal exhibiting a signal response signature for neutrons from a radioactive source. A system according to one embodiment includes an organic crystal comprising diphenylacetylene and stilbene or a stilbene derivative, the crystal having physical characteristics of formation from solution, the organic crystal exhibiting a signal response signature for neutrons from a radioactive source; and a photodetector for detecting the signal response of the organic crystal. Methods of making such crystals are also provided.

27 Claims, 5 Drawing Sheets

(56) References Cited

U.S. PATENT DOCUMENTS

| | | | |
|---|---|---|---|
| 5,976,076 A | 11/1999 | Kolff et al. |
| 5,997,472 A | 12/1999 | Bonnell et al. |
| 6,169,289 B1 | 1/2001 | White et al. |
| 6,269,169 B1 | 7/2001 | Funk et al. |
| 6,413,267 B1 | 7/2002 | Dumoulin-White et al. |
| 6,462,770 B1 | 10/2002 | Cline et al. |
| 6,477,403 B1 | 11/2002 | Eguchi et al. |
| 6,529,769 B2 | 3/2003 | Zigler |
| 6,687,000 B1 | 2/2004 | White |
| 6,730,019 B2 | 5/2004 | Irion |
| 6,775,567 B2 | 8/2004 | Cable et al. |
| 6,949,069 B2 | 9/2005 | Farkas et al. |
| 6,975,898 B2 | 12/2005 | Seibel |
| 6,975,899 B2 | 12/2005 | Faupel et al. |
| 7,003,147 B2 | 2/2006 | Inoue |
| 7,016,717 B2 | 3/2006 | Demos et al. |
| 7,164,138 B2 | 1/2007 | McGregor et al. |
| 7,172,553 B2 | 2/2007 | Ueno et al. |
| 7,257,437 B2 | 8/2007 | Demos et al. |
| 7,930,516 B1 | 4/2011 | Jin et al. |
| 7,945,077 B2 | 5/2011 | Demos |
| 8,207,507 B2 | 6/2012 | Zaitseva et al. |
| 8,461,546 B2 | 6/2013 | Payne et al. |
| 2001/0030744 A1 | 10/2001 | Chang |
| 2003/0158470 A1 | 8/2003 | Wolters et al. |
| 2003/0232445 A1 | 12/2003 | Fulghum, Jr. |
| 2005/0020926 A1 | 1/2005 | Wiklof et al. |
| 2006/0086311 A1 | 4/2006 | Zagumennyi et al. |
| 2007/0175383 A1 | 8/2007 | Fukuda et al. |
| 2008/0017804 A1 | 1/2008 | Krishnamoorthy et al. |
| 2008/0267472 A1 | 10/2008 | Demos |
| 2011/0266643 A1 | 11/2011 | Engelmann et al. |
| 2011/0284755 A1 | 11/2011 | Stradins et al. |
| 2013/0181135 A1 | 7/2013 | Payne |

OTHER PUBLICATIONS

U.S. Appl. No. 13/601,918, filed Aug. 31, 2012.
U.S. Appl. No. 13/437,836, filed Apr. 2, 2012.
U.S. Appl. No. 13/439,780, filed Apr. 4, 2012.
Advisory Action from U.S. Appl. No. 13/736,898, dated Dec. 9, 2013.
Notice of Allowance and Fee(s) Due from U.S. Appl. No. 13/736,898, dated Jan. 13, 2014.
Peurrung, A. J., "Recent developments in neutron detection," 2000 Elsevier Science B.V., Nuclear Instruments and Methods in Physics Research A, vol. 443, 2000, pp. 400-415.
Brooks, F. D., "Development of Organic Scintillators," North-Holland Publishing Co., Nuclear Instruments and Methods, vol. 162, 1979, pp. 477-505.
Vijayan et al., "Growth, optical, thermal and mechanical studies of methyl 4-hydroxybenzoate single crystals," 2003 Elsevier B.V., Journal of Crystal Growth, vol. 256, 2003, pp. 174-182.
Varfolomeeva, V. N., et al., "Polarization Diagrams for the Fluorescence of Single Crystals of Salicylic Acid and Salicylates," Soviet Physics-Crystallography, vol. 13, No. 2, Sep.-Oct. 1968, pp. 209-211.
Mandshukov, I. G., et al., "Properties of a New Class of Organic Scintillators: Derivatives of Salicyclic Acid," 1982 Plenum Publishing Corporation, University of Sofia, Bulgaria, Translated from Pribory i Tekhnika Eksperimenta, No. 3, May-Jun. 1981, pp. 605-611.
Zhao et al., "Characteristics of large-sized Ce:YAG Scintillation crystal grown by temperature gradient technique," 2003 Elsevier B.V., Journal of Crystal Growth, vol. 253, 2003, pp. 290-296.
Non-Final Office Action from U.S. Appl. No. 12/418,434, dated May 20, 2011.
Non-Final Office Action from U.S. Appl. No. 12/418,434 dated Nov. 22, 2011.
Notice of Allowance and Fee(s) Due from U.S. Appl. No. 12/418,434 dated Feb. 23, 2012.
Non-Final Office Action from U.S. Appl. No. 12/418,450 dated Jul. 13, 2011.
Non-Final Office Action from U.S. Appl. No. 12/418,450 dated Nov. 15, 2011.
Final Office Action from U.S. Appl. No. 12/418,450 dated Feb. 24, 2012.
Notice of Allowance and Fee(s) Due from U.S. Appl. No. 12/418,450 dated Oct. 22, 2012.
Non-Final Office Action from U.S. Appl. No. 13/736,898 dated Mar. 8, 2013.
Anutgan et al., "Effect of heat treatment on the stress and structure evolution of plasma deposited boron nitride thin films," Surface & Coatings Technology, vol. 202, 2008, pp. 3058-3066.
Dusane, R. O., "Opportunities for new materials synthesis by hot wire chemical vapor process," Thin Solid Films, vol. 519, 2011, pp. 4555-4560.
Lattemann et al., "New approach in depositing thick, layered cubic boron nitride coatings by oxygen addition-structural and compositional analysis," Thin Solid Films, vol. 515, 2006, pp. 1058-1062.
Bello et al., "Deposition of thick cubic boron nitride films: The route to practical applications," Diamond & Related Materials, vol. 14, 2005, pp. 1154-1162.
He et al., "Improvement of adhesion of cubic boron nitride filsm: effect of interlayer and deposition parameters," Materials Science Forum, vols. 475-479, 2005, pp. 3637-3638.
Shultis et al., "Efficiencies of Coated and Perforated Semiconductor Neutron Detectors," 2004 IEEE, pp. 4569-4574.
McGregor et al., "New Surface Morphology for Low Stress Thin-Film-Coated Thermal Neutron Detectors," 2002 IEEE, IEEE Transactions on Nuclear Science, vol. 49, No. 4, Aug. 2002, pp. 1999-2004.
Matsumoto et al., "The introducing of fluorine into the deposition of BN: a successful method to obtain high-quality, thick cBN films with low residual stress," Diamond and Related Materials, vol. 10, 2001, pp. 1868-1874.
Karim et al., "Effect of deposition parameters on the formation of cubic BN films deposited by plasma-assisted chemical vapour deposition from non-toxic material," Surface and Coatings Technology, vol. 54-55, 1992, pp. 355-359.
Notice of Allowance and Fee(s) Due from U.S. Appl. No. 13/439,780 dated Jul. 31, 2013.
Restriction/Election Requirement from U.S. Appl. No. 12/167,104 dated Jun. 8, 2011.
Non-Final Office Action from U.S. Appl. No. 12/167,104 dated Sep. 15, 2011.
Final Office Action from U.S. Appl. No. 12/167,104 dated Feb. 23, 2012.
Notice of Allowance and Fee(s) Due from U.S. Appl. No. 12/167,104 dated Jun. 21, 2012.
Udagawa et al., "Aberrant Porphyrin Metabolism in Hepatocellular Carcinoma," 1984 Academic Press, Inc., Biochemical Medicine, vol. 31, pp. 131-139.
Pitts et al., "Autofluorescene characteristics of immortalized and carcinogen-transformed human bronchial epithelial cells," 2001 SPIE, Journal of Biomedical Optics, vol. 6, No. 1, Jan. 2001, pp. 31-40.
Zawirska, B., "Comparative Porphyrin Content in Tumors with Contiguous Non-Neoplastic Tissues," 1979, Neoplasma, vol. 26, No. 2, pp. 223-229.
Malik et al., "Destruction of Erythroleukaemic Cells by Photoactivation of Endogenous Porphyrins," The Macmillan Press Ltd., 1987, Br. J. Cancer, 1987, vol. 56, pp. 589-595.
Zhang et al., "Far-red and NIR Spectral Wing Emission from Tissues under 532 and 632 nm Photo-excitation," 1999 OPA, Lasers in the Life Sciences, vol. 9, pp. 1-16.
Alfano et al., "Laser Induced Fluorescence Spectroscopy from Native Cancerous and Normal Tissue," 1984 IEEE, IEEE Journal of Quantum Electronics, vol. QE-20, No. 12, Dec. 1984, pp. 1507-1511.

(56) References Cited

OTHER PUBLICATIONS

Navone et al., "Heme Biosynthesis in Human Breast Cancer-Mimetic "In Vitro" Studies and Some Heme Enzymic Activity Levels," 1990 Pergamon Press Pic, International Journal on Biochemistry, vol. 22, No. 12, pp. 1407-1411.

Richards-Kortum et al., "Spectroscopic Diagnosis of Colonic Dysplasia," 1991 Pergamon Press Pic, Photochemistry and Photobiology, vol. 53, No. 6, pp. 777-786.

Demos et al., "Subsurface Imaging Using the Spectral Polarization Difference Technique and NIR Illumination," Part of the SPIE Conference on Optical Tomography and Spectroscopy of Tissue III, Jan. 1991, SPIE 3597, pp. 406-410.

Demos et al., "Tissue Imaging for Cancer Detection Using NIR Autofluorescence," 2002 SPIE, Optical Biopsy IV, Proceedings of SPIE, vol. 4613, pp. 31-34.

Corle et al., "Chapter 2—Instruments," Confocal Scanning Optical Microscopy and Related Imaging Systems, 1996, pp. 67-145.

SOLUTION-GROWN CRYSTALS FOR NEUTRON RADIATION DETECTORS, AND METHODS OF SOLUTION GROWTH

RELATED APPLICATIONS

This application is a continuation-in-part of U.S. patent application Ser. No. 12/418,434 to Zaitseva et al., filed Apr. 3, 2009, from which priority is claimed and which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF IRE INVENTION

The present invention relates to radiation detection, and more particularly to solution-grown crystals for neutron radiation detectors and related methods.

BACKGROUND

Pulse shape discrimination (PSD) of organic scintillators involves subtle physical phenomena which give rise to the delayed luminescence characteristic of neutrons, providing a means of distinguishing neutrons from the preponderance of prompt luminescence arising from background gamma interactions. The mechanism by which this occurs begins with intersystem crossing (ISC), where the excited singlet state (S1) nonradiatively relaxes to the excited triplet (T), as shown in FIG. 1. In FIG. 1, the basic physical processes leading to the delayed fluorescence characteristic of neutron excitation of organics with phenyl groups is shown.

Since the triplet is known to be mobile in some compounds, the energy migrates until two triplets collide and experience an Auger upconversion process, shown as Equation 1:

$$T_1 + T_1 \rightarrow S_0 + S_1 \qquad \text{Equation 1}$$

In Equation 1, $T_1$ is a triplet, $S_0$ is the ground state, and $S_1$ is a first excited state. Finally, the delayed singlet emission occurs with a decay rate characteristic of the migration rate and concentration of the triplet population, which is represented as Equation 2:

$$S_1 \rightarrow S_0 + h\nu \qquad \text{Equation 2}$$

In Equation 2, hv is fluorescence, while $S_0$ is the ground state and $S_1$ is a first excited state. The enhanced level of delayed emission for neutrons arises from the short range of the energetic protons produced from neutron collisions (thereby yielding a high concentration of triplets), compared to the longer range of the electrons from the gamma interactions. The resulting higher concentration of triplets from neutrons, compared to gamma interactions, leads to the functionality of PSD. The observation of PSD is believed to be in part related to the benzene ring structure, allowing for the migration of triplet energy.

It is generally accepted in the prior art that stilbene offers good PSD. However, stilbene is notoriously difficult to obtain due in part to its standard formation by melt growth. It is presently believed that the expensive melt growth process is a superior process able to create large enough crystals for use as large-crystal scintillators, e.g., in single-crystal radiation detectors, etc. The limited availability of stilbene and other melt grown crystals coupled with their high cost presents a serious challenge to radiation detector development.

Accordingly, it would be beneficial to grow organic scintillator crystals, including stilbene and other types of crystals, using solution growth, which should thereby increase access to such materials as well as significantly reduce their cost.

SUMMARY

A method according to one embodiment includes growing an organic crystal from solution, the organic crystal exhibiting a signal response signature for neutrons from a radioactive source, wherein the crystal includes diphenylacetylene (DPAC) and stilbene or a stilbene derivative.

A system according to one embodiment includes an organic crystal comprising diphenylacetylene and stilbene or a stilbene derivative, the crystal having physical characteristics of formation from solution, the organic crystal exhibiting a signal response signature for neutrons from a radioactive source; and a photodetector for detecting the signal response of the organic crystal.

An organic crystal according to another embodiment includes an organic crystal comprising diphenylacetylene and stilbene or a stilbene derivative, the crystal having physical characteristics of formation from solution, the organic crystal exhibiting a signal response signature for neutrons from a radioactive source.

Other aspects and embodiments of the present invention will become apparent from the following detailed description, which, when taken in conjunction with the drawings, illustrate by way of example the principles of the invention.

DETAILED DESCRIPTION

Figure 1:
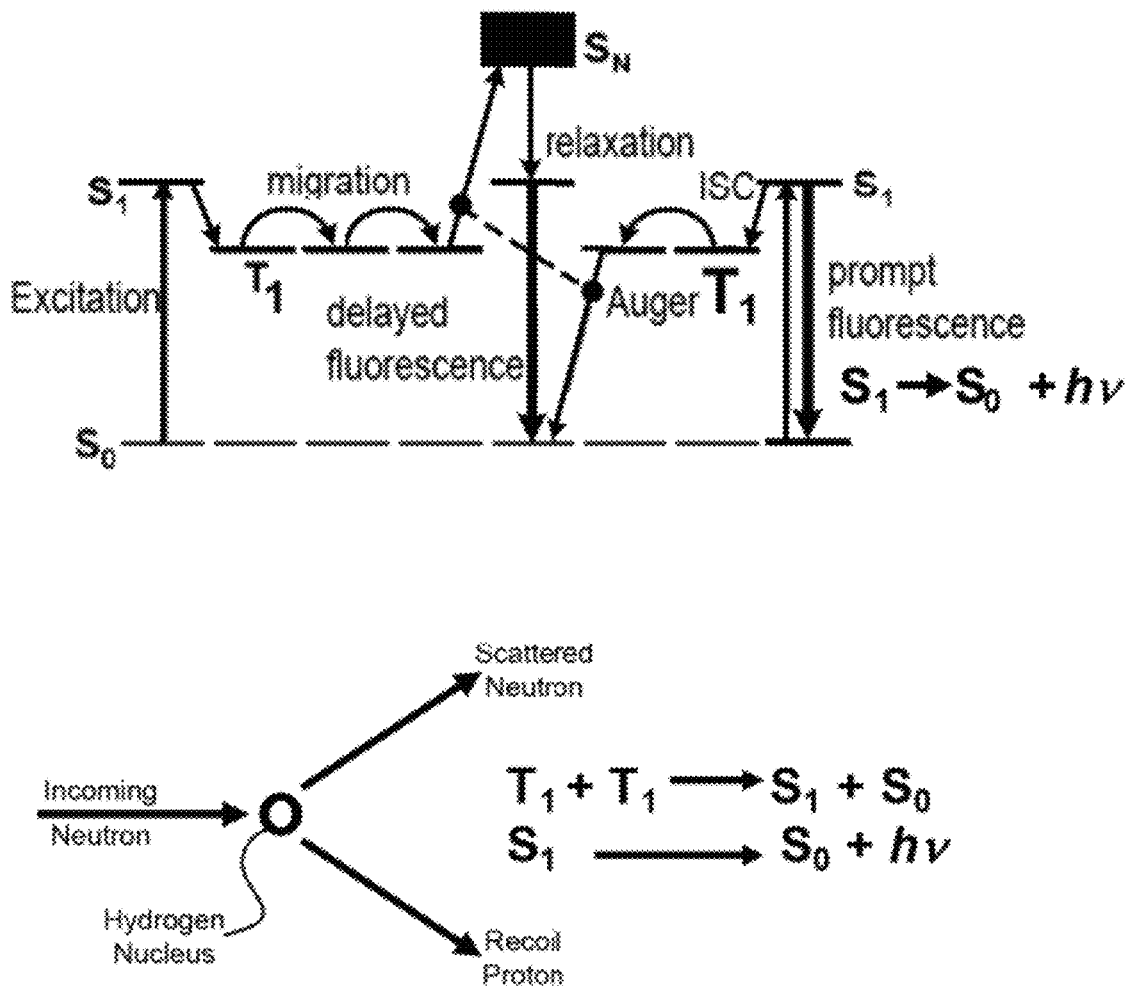
FIG. 1 shows a mechanism for delayed photoluminescence according to the prior art.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description describes several illustrative embodiments for growing organic scintillator crystals in solution and the resultant products, as well as systems incorporating such crystals.

An organic crystal according to one embodiment includes an organic crystal comprising diphenylacetylene and stilbene or a stilbene derivative, the crystal having physical characteristics of formation from solution, the organic crystal exhibiting a signal response signature for neutrons from a radioactive source.

A system according to another embodiment includes an organic crystal comprising diphenylacetylene and stilbene or a stilbene derivative, the crystal having physical characteristics of formation from solution, the organic crystal exhibiting a signal response signature for neutrons from a radioactive source; and a photodetector for detecting the signal response of the organic crystal.

A method according to yet another embodiment includes growing an organic crystal from solution, the organic crystal exhibiting a signal response signature for neutrons from a radioactive source, wherein the crystal includes diphenylacetylene and stilbene or a stilbene derivative.

As noted above, some organic crystals demonstrate a scintillation response to radiation of various types. This property makes such organic crystals useful for radiation detection. However, growth of such crystals by solution growth has heretofore been unknown. Following are several embodiments describing solution growth methodology and products. Some of the most sought after characteristics for candidate solution-grown organic crystals include:

1) High hydrogen content for interactions with neutrons.
2) Components including low-Z constituents, such as H, C, N, F, and O, to avoid excessive gamma interaction.
3) Inclusion of phenyl rings that fluoresce efficiently from the singlet state and also exhibit delayed emission for PSD.
4) Crystals that can be grown from common solvents (such as water, alcohol, toluene, etc.) for low-cost production.
5) Materials that have acceptable fragility and hygroscopicity (e.g., low sensitivity to moisture).

Several new materials with PSD properties approaching that of stilbene have been identified. Among these discovered materials, the most promising scintillators include 1-1-4-4-tetraphenyl-1-3-butadiene, 2-fluorobiphenyl-4-carboxylic acid, 9-10-diphenylanthracene, and 1-3-5-triphenylbenzene which, in addition, have been found to be easily grown from solution.

The decay from heavier particles such as fast neutrons (imparting energy to protons) and alphas, lead to the emergence of a long decay component as a signature of the interaction. Gamma rays transfer their energy to electrons, which are much lighter and therefore have a greater stopping length and give rise to a far lower energy density in a material and a reduced long decay component.

Figure 2A:
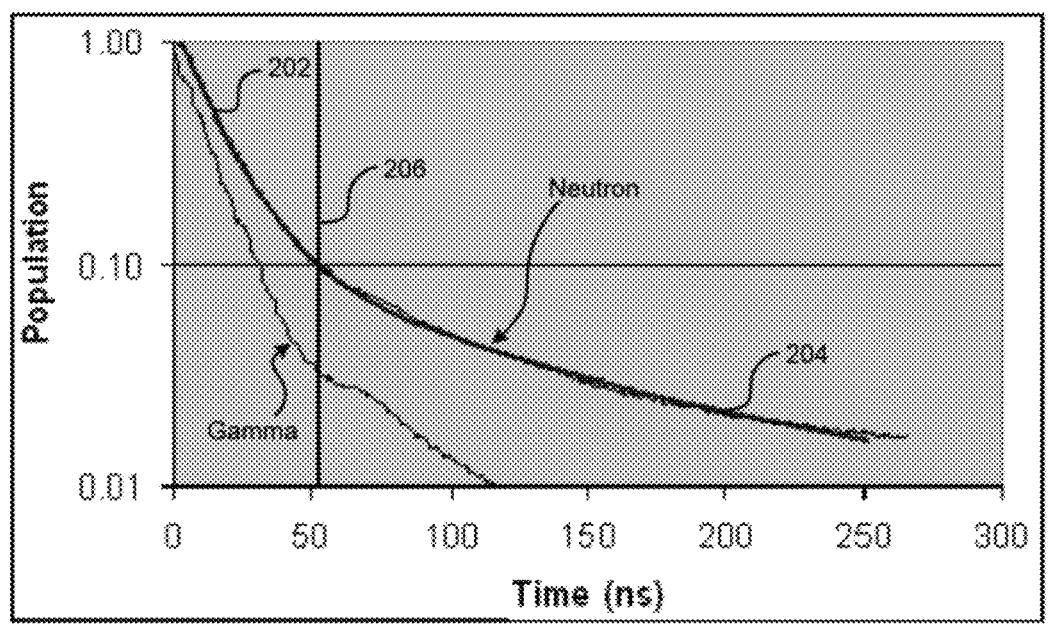
FIG. 2A shows a plot of Population versus Time for stilbene according to one embodiment.

From measurements taken during the course of experiments, the differences in decay shapes are apparent. In FIG. 2A, a plot of logarithmic population versus linear tune (ns) for stilbene is shown. Population can be referred to as the output of light from a test crystal under examination, in this case a stilbene crystal, after the crystal has light input to it. As can be seen from the plot, some light is produced by the crystal almost immediately, referred to as a burst of light, and other light is produced by the crystal over a period of time, referred to as delayed light. Generally, the plot for each type of radiation will have a steep component 202 and a tail component 204, where the differentiation point 206 between the two is defined in the region where the slope of the line changes dramatically. The upper line in the plot is a Neutron light decay, while the lower line is a Gamma light decay. As can be seen, stilbene is able to differentiate between the Neutron and Gamma light decays, and produces noticeably different lines for each radiation type. However, not every compound has this ability to separate between Gamma and Neutron light decay, and therefore compounds which do are very useful for PSD, as Gamma and Neutron light decay plots have different pulse shapes.

Figure 2B:
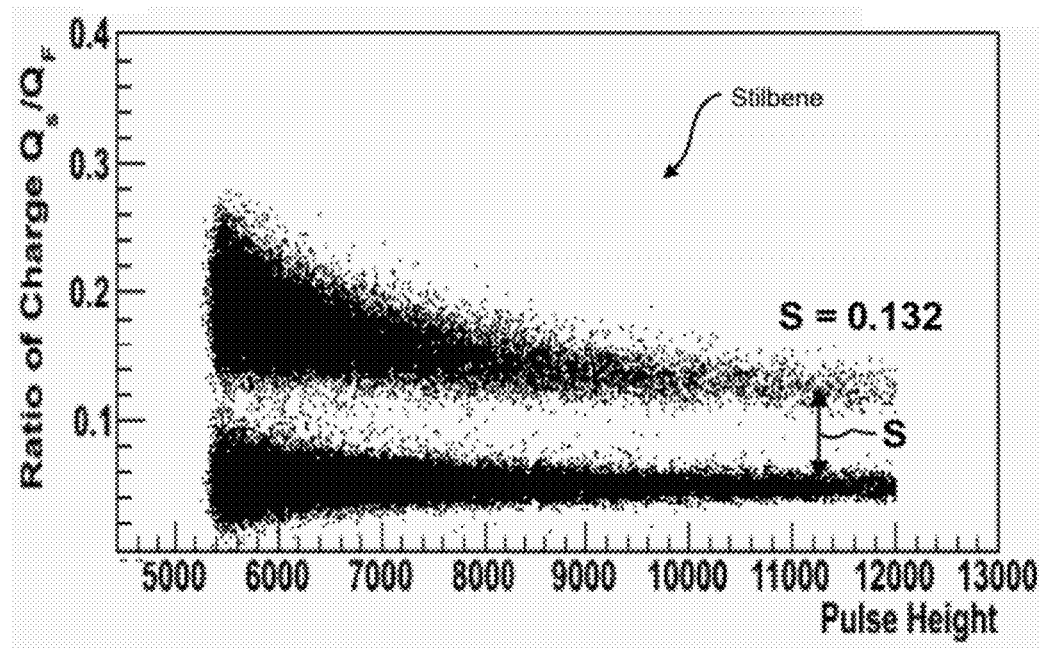
FIG. 2B shows a PSD plot for stilbene of the ratio of charge from delayed emission versus pulse height.

It can also be seen that the shape for the neutron response has a long component, while gammas only have a short time component. These decays can be digitally captured, and then the ratio of the area of the long time component (e.g., for >50 nsec) with that of the area of the entire waveform can be plotted versus pulse height. By doing this, a plot of this ratio against the total area can be generated to differentiate between interactions with neutrons and gammas. The plot shown in FIG. 2B reveals how this method of digital pulse-shape discrimination can separate the neutron and gamma absorption events encountered by stilbene. Now referring to FIG. 2B, to test for PSD properties, the existence of two regions of response reveals the presence of both neutrons (upper scatter points) and gammas (lower scatter points) in a plot of the ratio of change ($Q_S/Q_F$) versus the pulse height. The larger this separation, S, the better the organic crystal is at PSD for distinguishing gammas and neutrons. For reference, the plot indicates that stilbene has a mean separation of 0.132. As can be seen, stilbene is able to differentiate between the Neutron and Gamma light decays, and produces noticeably different lines for each radiation type. However, not every compound has this ability to separate between Gamma and Neutron light decay, and therefore compounds which do are very useful for PSD, as Gamma and Neutron light decay plots have different pulse shapes. Stilbene may be used to compare the PSD properties of candidate organic crystals.

Figure 2C:
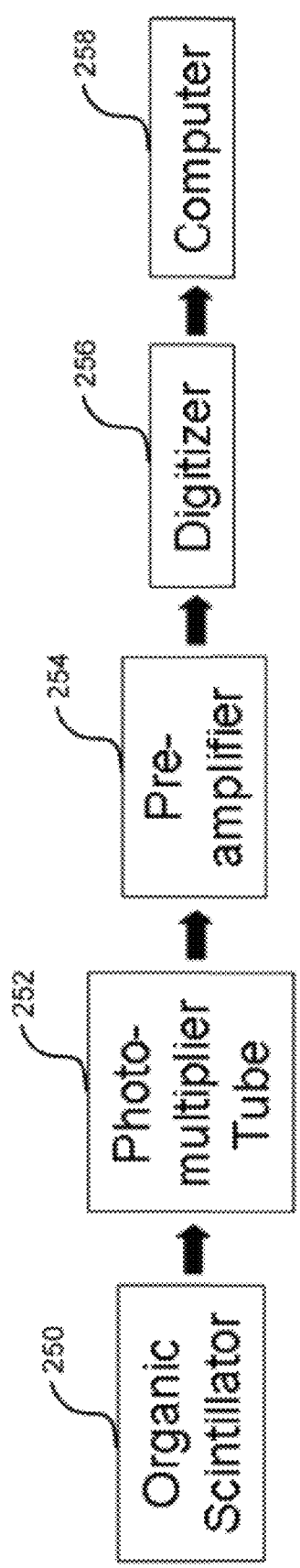
FIG. 2C shows a simplified layout of an instrument according to one embodiment.

A simplified schematic layout of an instrument is shown in FIG. 2C according to one embodiment, where light from the organic scintillator 250 may be sensed by a photodetector, such as a photomultiplier tube 252, then amplified e.g., by a preamplifer 254, digitized e.g., by an analog to digital converter 256, and numerically processed by a computer 258 to calculate the PSD. This methodology can be applied to data collected for any organic crystal to obtain plots that can be interpreted to determine PSD properties. This type of signal analysis can also be accomplished with analog electronics.

According to one embodiment, a method includes growing an organic crystal from solution, the organic crystal exhibiting a signal response signature for neutrons from a radioactive source. In some embodiments, the solution which the organic crystal is grown from may be comprised of a solvent and a solute.

Preferred solvents include common solvents such as water, alcohol, and toluene, though other solvents can be used. In illustrative approaches, the solution may include at least one of water, an alcohol, an ether, an ester, and a derivative of benzene. The solvent may comprise more than 10% of the solution by volume or by weight, and in some approaches more than 30% of the solution.

Many types of materials may form the solute that can be grown into an organic crystal, including those that generate a signal response for neutrons, and may be combined in various embodiments.

Some exemplary materials include 1,3,5-triphenyl benzene, 1-1-4-4-tetraphenyl-1,3-butadiene, 1-4-diphenyl-1-3-butadiene, 9,10-diphenylanthracene, 9-phenylanthracene, diphenylacetylene, 2-fluorobiphenyl-4-carboxylic acid, 4-biphenylcarboxylic acid, and n-phenylanthranilic acid. In some further embodiments, the organic crystal may include a material selected from a group consisting of 1-3-5-triphenyl benzene, 1-1-4-4-tetraphenyl-1-3-butadiene, 1-4-diphenyl-1-3-butadiene, 9-10-diphenyl-anthracene, 9-phenylanthracene, diphenylacetylene, 2-fluorobiphenyl-4-carboxylic acid, 4-biphenylcarboxylic acid, and n-phenylanthranilic acid. It should be kept in mind that the foregoing list is nonexclusive.

In some approaches, the organic crystal may include one or more benzene and/or phenyl rings. Generally, only a lone benzene ring is referred to as benzene, while a benzene ring with another group is referred to as a phenyl ring. Some exemplary materials which include one or more benzene and/or phenyl rings include benzene, phenyl, salicylamide, tetraphenylbutadiene, triphenylbenzene, etc.

In more approaches, the organic crystal may include stilbene or a stilbene derivative. For example, stilbene may be included in the grown organic crystal to take advantage of the PSD properties of stilbene. This allows for readily available growth techniques to produce large quantities of organic crystals including the PSD properties of stilbene, without the drawbacks of long wait times and/or high costs needed to obtain stilbene from distributors.

In still more approaches, the organic crystal includes a salt of an aromatic acid. For example, a salt of an aromatic acid may include ammonium salicylate, sodium salicylate, etc. In further approaches, the organic crystal may include lithium salt of an aromatic acid, such as a lithium salt of 2-fluorobiphenyl-4-carboxylic acid.

In one approach, the organic crystal may include lithium salicylate.

In various approaches, the solution may be held at a temperature that is less than that of the melting point of the solvent and/or solute during the growing. Illustrative approaches include growing the organic crystal by solvent evaporation at a constant temperature held between about 25° C. and about 100° C., or by temperature reduction within the range between about the boiling and freezing points of a corresponding solvent.

According to some approaches, the organic crystal may have a length of greater than about 1 mm in one dimension. For example, the organic crystal may have dimensions of 1.1 mm×0.5 mm×0.7 mm. In more approaches, the organic crystal may have a length of greater than about 5 mm in one dimension, and in even more approaches, the organic crystal may have a length of greater than about 25 mm in one dimension. Of course, organic crystals with more or less length in one dimension may be used with the present method.

In some preferred embodiments, the signal response signature may include a time-delayed luminescence characteristic of neutrons interacting with the organic crystal relative to a luminescence characteristic of gamma rays interacting with the organic crystal.

Any of the methods described above may be included in one or more systems. For example, a system may include an organic crystal having physical characteristics of formation from solution, the organic crystal exhibiting a signal response signature for neutrons from a radioactive source. The system may further include a photodetector for detecting the signal response of the organic crystal. This system may be useful for detection of radioactive substances, determination of the strength of radioactive emanations from a radioactive substance, etc.

In some embodiments, the organic crystal used in the system may exhibit faceted growth typical of solution growth on the faces of the organic crystal.

In more approaches, the organic crystal may include one or more benzene and/or phenyl rings. Any of the materials described above may be used in the system as well.

In more approaches, the organic crystal may include stilbene, may include a derivative of stilbene, and/or may include a material selected from a group consisting of 1-3-5-triphenyl benzene, 1-1-4-4-tetraphenyl-1-3-butadiene, 1-4-diphenyl-1-3-butadiene, 9-10-diphenyl-anthracene, 9-phenylanthracene, diphenyl acetylene, 2-fluorobiphenyl-4-carboxylic acid, 4-biphenylcarboxylic acid, and n-phenylanthranilic acid.

In some approaches, the organic crystal may include a salt of an aromatic acid. In further approaches, the organic crystal may include lithium salt of an aromatic acid. Also, the organic crystal may include lithium salicylate.

In even more embodiments, the organic crystal may have a length of greater than about 1 mm in one dimension, a length of greater than about 5 mm in one dimension, a length of greater than about 25 mm in one dimension, etc. Of course, the organic crystal may have a length in one dimension of greater than or less than the dimensions described herein.

The signal response signature, according to some preferred embodiments, may include a delayed luminescence characteristic of neutrons interacting with the organic crystal relative to a luminescence characteristic of gamma rays interacting with the organic crystal.

Also, the system may further comprise a processor for processing an output of the photodetector using pulse shape discrimination for differentiating responses for neutrons and gamma irradiation.

In another embodiment of an organic crystal, the organic crystal comprises an organic crystal having physical characteristics of formation from solution. Also, the organic crystal exhibits a signal response signature for neutrons from a radioactive source. The organic crystal also has a length of greater than about 1 mm in one dimension.

In some more embodiments, the organic crystal may include one or more benzene and/or phenyl rings. Also, the organic crystal may include a material selected from a group consisting of 1-3-5-triphenyl benzene, 1-1-4-4-tetraphenyl-1-3-butadiene, 1-4-diphenyl-1-3-butadiene, 9-10-diphenyl-anthracene, 9-phenylanthracene, diphenyl acetylene, 2-fluorobiphenyl-4-carboxylic acid, 4-biphenylcarboxylic acid, and n-phenylanthranilic acid.

In more embodiments, the organic crystal may include a salt of an aromatic acid and/or a lithium salt of an aromatic acid.

In more approaches, the organic crystal may have a length of greater than about 5 mm in one dimension, more preferably greater than about 25 mm in one dimension.

Illustrative compounds for scintillator use, including at least some of those materials herein, are described in U.S. patent application Ser. No. 12/418,450 to Zaitseva et al., having title "Compounds for Neutron Radiation Detectors and Systems Thereof," filed Apr. 3, 2009, and which is herein incorporated by reference.

EXPERIMENTS

Experiment 1

Solution Growth by Slow Evaporation

Figure 3A:
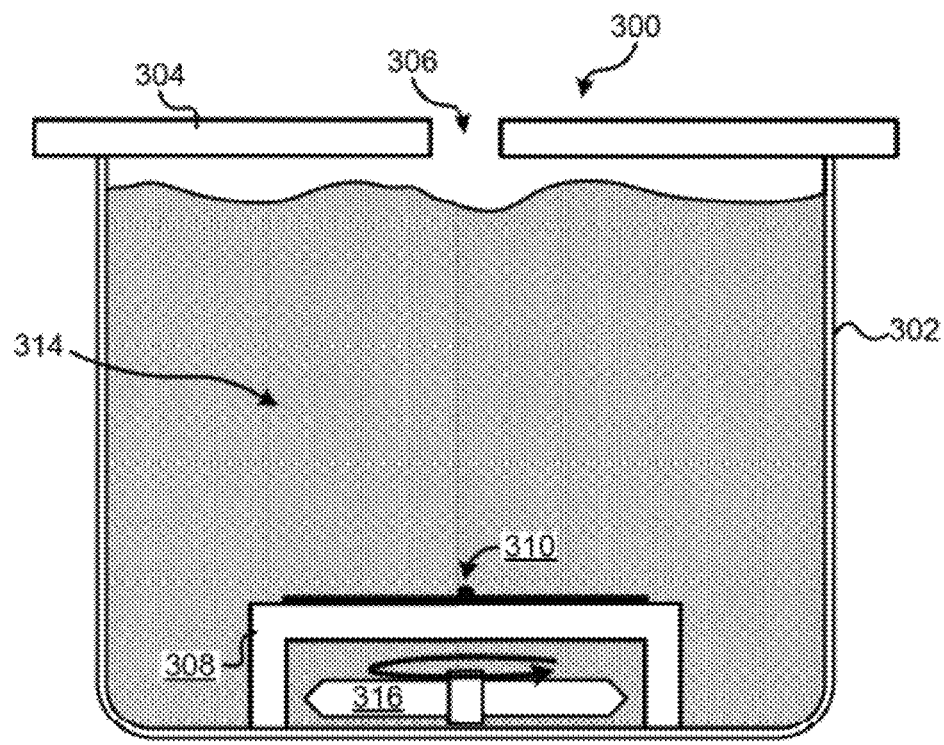
FIG. 3A shows a general schematic of a crystallizer before evaporation of a growth solution according to one embodiment.

The first experiment involved growing a single stilbene crystal in solution. All components of the raw materials used for the crystal growth in the first experiment had a purity of not lower than 98%. Crystal growth was conducted in a 2 L glass crystallizer 300, as shown in FIG. 3. The crystallizer 300 included a growth tank 302, and a lid 304 which included an evaporation hole(s) 306. Also, the crystallizer 300 included a platform 308 which was positioned to accept a crystal seed 310. In this experiment, an initial stilbene seed 310 with dimensions of about 2.0 mm×2.0 mm×5.0 mm was mounted in the middle of a Teflon platform 308 installed near the bottom of the crystallizer 300. The crystallizer 300 included a growth solution 314, which was prepared from 226 g of the stilbene powder mixed with 1774 g of anhydrous toluene, which corresponds to the saturation point of 25° C. The solution 314 was heated in a glass flask with a magnetic stirrer until the powder completely dissolved. The solution 314 was then filtered and left with continuous stirring at 40° C. After two days of overheating, the solution 314 was cooled to 30° C., transferred to the crystallizer 300, cooled to about 25° C. (room temperature), and left for slow evaporation with continuing magnetic stirring, provided by magnetic stirrer 316.

Figure 3B:
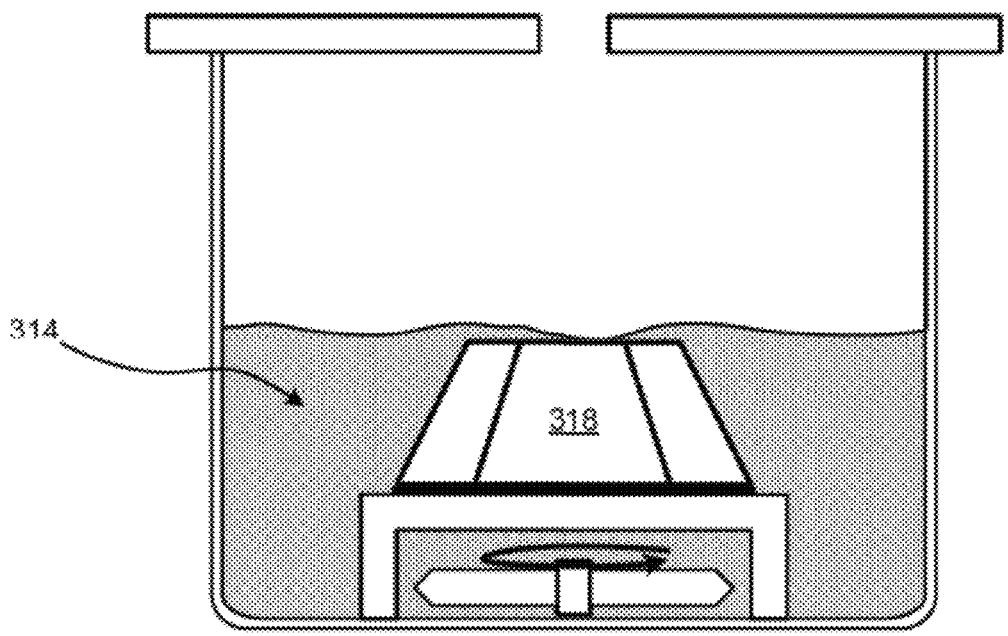
FIG. 3B shows a general schematic of a crystallizer after evaporation of a growth solution according to one embodiment.

Now referring to FIG. 3B, the crystal 318 was removed when it grew in height close to the level of the growth solution 314, thereby not altering the growth of the crystal 318 by exposing one surface to a non-solution environment.

In order to grow crystals of other compounds, the initial concentration of the growth solution was changed in accordance with the solubility of the compounds measured at room temperature (about 25° C.). For example, Table 1 below lists crystal compounds and the corresponding masses of materials used for crystal growth in the slow evaporation experiments.

TABLE 1

Component Masses for Crystal Growth

| Crystal Compound | Mass of Powder | Mass of Solution |
|---|---|---|
| 1-3-5-Triphenylbenzene | 177 g of triphenylbenzene | 1823 g of toluene |
| 1-1-4-4-tetraphenyl-1-3-butadiene | 48 g of tetraphenylbutadiene | 1952 g of toluene |
| 9-10-diphenylanthracene | 68 g of diphenylanthacene | 1932 g of toluene |
| Diphenylacetylene | 1246 g of diphenylacetylene | 754 g of toluene |

Experiment 2

Solution Growth by Temperature Reduction

Figure 4:
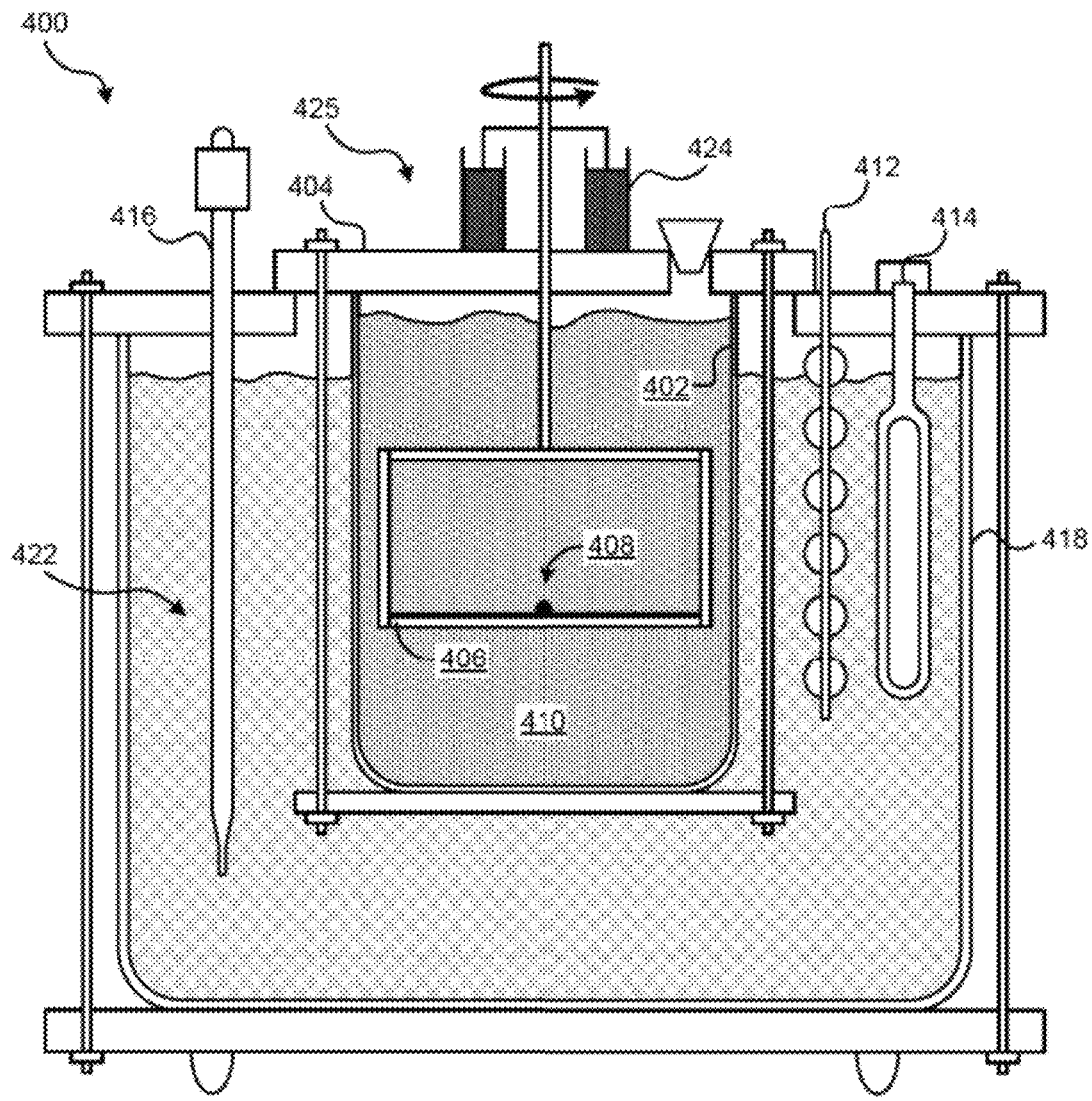
FIG. 4 shows a general schematic of a crystallizer in a water bath according to one embodiment.

The second experiment involved growing a single stilbene crystal. Crystal growth was conducted in a 1 L glass crystallizer placed in a thermo-stabilizing water bath 400, as shown in FIG. 4. The crystallizer 420 included a growth tank 402, an air-sealed lid 404, a platform 406 for holding a crystal seed 408, and growth solution 410 for growth of the crystal. The apparatus 400 also included a water bath for stabilizing the temperature of the crystallizer 425. The water bath included a water tank 418 at least partially filled with water 422 or some other liquid, a stirrer 412, a heater 414, a thermocontroller 416, and an air-sealed lid 420. The platform 406 in the crystallizer 425 was rotatable, and the upper seal was maintained with an oil cup seal 424.

In this case, an initial stilbene seed 408 with dimensions of about 2.0 min×2.0 mm×5.0 mm was mounted in the middle of a Teflon platform 406 that was capable of being rotated at 30 RPM, with 15 second periods in a reverse direction. The growth solution 410 was prepared from 242 g of a stilbene powder mixed with 758 g of anhydrous toluene, which corresponds to the initial saturation point of 50° C. The solution 410 was heated in a glass flask with a magnetic stirrer until complete dissolution of the powder, then filtered and left with continuous stirring at 65° C. After two days of overheating, the solution 410 was cooled to 57° C., transferred to the crystallizer 425 containing the stilbene seed 408 which was also pre-heated at 57° C. The system 425 was left without heating until the temperature reached 50° C., when the reversible rotation was turned on. The crystal growth was conducted by the gradual decrease of the temperature to maintain a vertical growth rate of about 1 mm/day, until room temperature (about 25° C.) was reached. After that, the crystal was removed from the solution.

In order to grow crystals of other compounds, the initial concentration of the growth solution was changed in accordance with the solubility of the compounds measured at the initial saturation point of 50° C. For example, Table 2 below lists crystal compounds and the corresponding masses of materials used for crystal growth in the temperature reduction experiments.

TABLE 2

Component Masses for Crystal Growth

| Crystal Compound | Mass of Powder | Mass of Solution |
|---|---|---|
| 1-3-5-Triphenylbenzene | 144 g of triphenylbenzene | 856 g of toluene |
| 1-1-4-4-tetraphenyl-1-3-butadiene | 55 g of tetraphenylbutadiene | 945 g of toluene |

Experiment 3

To determine whether organic crystals that had previously been untested for PSD properties could be used as scintillators, 60 initial sub-millimeter-size test crystals of organic compounds were evaluated for photoluminescence (PL). The PL was compared based on approximate five-level rating, with 0-level corresponding to practically non-luminescent compounds, and 5-level corresponding to the highest intensity, which was found in p-terphenyl and tetraphenylbutadiene (according to this scale, stilbene was rated as 4).

Also, all efficiently luminescent compounds were selected for further crystal growth, radio-luminescence and pulse-shape discrimination (PSD) tests. Of the initial 60 candidate materials, only 50 survived to this step of testing. These 50 candidate organic crystals were grown from solution to a size of about 0.1 mm to about 1 mm. Each crystal's luminescence properties were evaluated to down-select ten candidates with highest scintillation efficiency of not less than 0.5 of the scintillation efficiency of solid stilbene (used as a reference material).

It was surprisingly found that some solution-grown organic crystals have scintillation efficiency not only close to, but even exceeding that of stilbene. At the same tune, the results of the measurements indicated that the light yield produced by the solution-grown organic crystals is substantially influenced by the impurities incorporated during the growth. This result shows that the precise comparison of the light yield in new materials can be done with extremely pure materials which can be obtained through multiple re-crystallization procedures.

In re-crystallization, the crystals are formed, then removed from the solution. The crystals are then placed in a new volume of solvent, where they are dissolved then re-crystallized. Since a large fraction of the initial raw materials might be discarded during such procedures, the re-crystallization may increase the cost of the chemicals, as well as the time required to form individual compounds.

PSD measurements were made for neutron detection with small (about 0.5 mm to about 5 mm) organic crystals. Test measurements made with stilbene crystals showed that crystalline powder with a grain size of about 0.5 mm to about 1 mm is sufficient for preliminary (qualitative) detection of PSD.

Of course, these experiments are included as examples only, and are not meant to limit the scope of the invention in any way. The experiments conducted are reported to provide examples of how the crystal growth has been carried out in successful environments. Many other embodiments of growing crystals may be possible, and are only to be limited by the scope of the claims.

According to some embodiments of the invention, many beneficial uses may be derived. For example, some embodiments may be useful for detection of illicit nuclear weapons at ports of entry, at security checkpoints, at sensitive city installations, in scanning equipment for wide area sweeping, at off shore facilities, on ships and/or boats, etc. Some embodiments may be useful for monitoring of nuclear power plants for dangerous and/or unhealthy levels of radiation, for leakage detection, etc. Also, some embodiments may be used for the measurement of neutrons emanating from special nuclear material, possibly by further using coincidence detection (registering the nuclear multiplicity) and/or on the basis of active interrogation methods. Also, some embodiments may be used for scientific measurements of neutron emitters, such as in laboratory or classroom settings.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. An organic crystal, comprising:
   an organic crystal comprising diphenylacetylene and stilbene or a stilbene derivative, the crystal having physical characteristics of formation from solution, the organic crystal exhibiting a signal response signature for neutrons from a radioactive source.

2. The organic crystal of claim 1, wherein the organic crystal includes one or more benzene or phenyl rings.

3. The organic crystal of claim 1, wherein the organic crystal includes a material selected from a group consisting of 1-3-5-triphenyl benzene, 1-1-4-4-tetraphenyl-1-3-butadiene, 1-4-diphenyl-1-3-butadiene, 9-10-diphenyl-anthracene, 9-phenylanthracene, diphenyl acetylene, 2-fluorobiphenyl-4-carboxylic acid, 4-biphenylcarboxylic acid, and n-phenylanthranilic acid.

4. The organic crystal of claim 1, wherein the organic crystal includes a salt of an aromatic acid.

5. The organic crystal of claim 1, wherein the organic crystal includes a lithium salt of an aromatic acid.

6. The organic crystal of claim 1, wherein the organic crystal includes a lithium salt of 2-fluorobiphenyl-4-carboxylic acid.

7. The organic crystal of claim 1, wherein the organic crystal has a length of greater than about 1 mm in one dimension.

8. The organic crystal of claim 1, wherein the organic crystal has a length of greater than about 5 mm in one dimension.

9. The organic crystal of claim 1, wherein the organic crystal has a length of greater than about 25 mm in one dimension.

10. The organic crystal of claim 1, said organic crystal exhibiting typical faceted growth on the faces of said crystal.

11. A system, comprising:
    an organic crystal comprising diphenylacetylene and stilbene or a stilbene derivative, the crystal having physical characteristics of formation from solution, the organic crystal exhibiting a signal response signature for neutrons from a radioactive source; and
    a photodetector for detecting the signal response of the organic crystal.

12. The system of claim 11, said organic crystal exhibiting typical faceted growth on the faces of said crystal.

13. The system of claim 11, wherein the organic crystal includes one or more benzene or phenyl rings.

14. The system of claim 11, wherein the organic crystal includes a material selected from a group consisting of 1-3-5-triphenyl benzene, 1-1-4-4-tetraphenyl-1-3-butadiene, 1-4-diphenyl-1-3-butadiene, 9-10-diphenyl-anthracene, 9-phenylanthracene, 2-fluorobiphenyl-4-carboxylic acid, 4-biphenylcarboxylic acid, and n-phenylanthranilic acid.

15. The system of claim 14, wherein said organic crystal includes a derivative of stilbene.

16. The system of claim 11, wherein the organic crystal includes a salt of an aromatic acid.

17. The system of claim 16, wherein the organic crystal includes lithium salt of an aromatic acid.

18. The system of claim 16, wherein the organic crystal includes lithium salicylate.

19. The system of claim 16, wherein the organic crystal includes a lithium salt of 2-fluorobiphenyl-4-carboxylic acid.

20. The system of claim 11, wherein the organic crystal has a length of greater than about 1 mm in one dimension.

21. The system of claim 11, wherein the organic crystal has a length of greater than about 5 mm in one dimension.

22. The system of claim 11, wherein the organic crystal has a length of greater than about 25 mm in one dimension.

23. The system of claim 11, wherein the signal response signature includes a delayed luminescence characteristic of neutrons interacting with the organic crystal relative to a luminescence characteristic of gamma rays interacting with the organic crystal.

24. The system of claim 11, further comprising a processor for processing an output of the photodetector using pulse shape discrimination for differentiating responses for neutrons and gamma irradiation.

25. A method, comprising:
    growing an organic crystal from solution, the organic crystal exhibiting a signal response signature for neutrons from a radioactive source, wherein the crystal includes diphenylacetylene and stilbene or a stilbene derivative.

26. The method of claim 25, said solution being comprised of a solvent and a solute, said solvent comprising more than 10% of said solution, and said solution being held at a temperature that is less than that of the melting point of said solvent during the growing.

27. The method of claim 25, wherein the organic crystal has a length of greater than about 1 mm in one dimension.

* * * * *